United States Patent
Tai (10) Patent No.: US 9,180,490 B2
(45) Date of Patent: Nov. 10, 2015

(54) ULTRASOUND TRANSDUCER AND METHOD FOR MANUFACTURING AN ULTRASOUND TRANSDUCER

(75) Inventor: Alan Chi-Chung Tai, Phoenix, AZ (US)

(73) Assignee: General Electric Company, Schenectady, NY (US)

(*) Notice: Subject to any disclaimer, the term of this patent is extended or adjusted under 35 U.S.C. 154(b) by 781 days.

(21) Appl. No.: 13/477,948

(22) Filed: May 22, 2012

(65) Prior Publication Data
US 2013/0315035 A1 Nov. 28, 2013

(51) Int. Cl.
*B06B 1/06* (2006.01)
*A61B 8/00* (2006.01)
*A61B 8/08* (2006.01)

(52) U.S. Cl.
CPC ............ *B06B 1/0622* (2013.01); *A61B 8/4494* (2013.01); *A61B 8/4461* (2013.01); *A61B 8/483* (2013.01); *Y10T 29/49005* (2015.01)

(58) Field of Classification Search
CPC .. Y10T 29/49005; A61B 8/4494; A61B 8/44; B06B 1/0622
USPC ............................................ 367/140; 29/594
See application file for complete search history.

(56) References Cited

U.S. PATENT DOCUMENTS

| | | | |
|---|---|---|---|
| 6,776,762 B2 * | 8/2004 | Erikson et al. | 600/459 |
| 2003/0018267 A1 * | 1/2003 | Erikson et al. | 600/459 |
| 2009/0294991 A1 | 12/2009 | Sudol et al. | |
| 2009/0309217 A1 | 12/2009 | Sudol | |
| 2010/0317972 A1 | 12/2010 | Baumgartner et al. | |
| 2011/0071397 A1 * | 3/2011 | Wodnicki et al. | 600/459 |

OTHER PUBLICATIONS

U.S. Appl. No. 13/398,692, filed Feb. 16, 2012.

* cited by examiner

*Primary Examiner* — Mark Hellner
(74) *Attorney, Agent, or Firm* — Dean D. Small; The Small Patent Law Group, LLC (57) ABSTRACT

An ultrasound transducer includes an array of acoustic elements, an integrated circuit, and an interposer. The interposer includes conductive elements for electrically connecting the acoustic elements to the integrated circuit. The conductive elements are electrically connected to the integrated circuit. Solder is engaged between the acoustic elements and the conductive elements of the interposer such that the conductive elements of the interposer are electrically connected to the acoustic elements through the solder.

18 Claims, 9 Drawing Sheets

ULTRASOUND TRANSDUCER AND METHOD FOR MANUFACTURING AN ULTRASOUND TRANSDUCER

BACKGROUND OF THE INVENTION

The subject matter disclosed herein relates generally to ultrasound systems, and more particularly to ultrasound transducers and methods for manufacturing ultrasound transducers.

Ultrasound systems typically include ultrasound scanning devices (e.g., an ultrasound transducer housed within a probe) that perform various ultrasound scans (e.g., imaging a body or other volume). The scanning devices include acoustic elements that transmit and receive ultrasound signals. The acoustic elements may be arranged in an array. The ultrasound signals received by the acoustic elements are used to generate an image of the body or other volume. For example, the received ultrasound signals may be used to generate an image of internal tissues of a patient, such as, but not limited to, an image of a patient's heart.

At least some known ultrasound systems include an interposer (e.g., a flex circuit) that is electrically and mechanically connected to the acoustic elements. The interposer extends between the acoustic elements and a thermal backing layer or electronics (e.g., one or more integrated circuits) that perform transmit and/or receive beamforming operations on the ultrasound signals. For example, the interposer may extend between the acoustic elements and beamforming electronics to provide an electrical connection between the acoustic elements and the beamforming electronics. Alternatively, and for example, the interposer extends between the acoustic elements and a thermal backing layer to mechanically connect the acoustic elements to the thermal backing layer. Some know interposers are cables that electrically connect the acoustic elements to one or more other components (e.g., an RF processor, a memory, a signal processor, a user input, beamforming electronics, a display, and/or the like) of the ultrasound system.

In some known ultrasound systems, an epoxy is used to mechanically connect or both mechanically and electrically connect the interposer to the acoustic elements. But, the mechanical connection provided by the epoxy may be susceptible to failure from environmental stresses. For example, the mechanical connection provided by the epoxy may fail when the ultrasound scanning device is exposed to water and/or other liquids over a period of time (e.g., when all or a portion of the ultrasound scanning device is soaked in water and/or another liquid). Failure of the mechanical connection between the acoustic elements and the interposer may electrically disconnect the interposer from the acoustic elements and thereby disrupt operation of the ultrasound system.

BRIEF DESCRIPTION OF THE INVENTION

In one embodiment, an ultrasound transducer includes an array of acoustic elements, an integrated circuit, and an interposer. The interposer includes conductive elements for electrically connecting the acoustic elements to the integrated circuit. The conductive elements are electrically connected to the integrated circuit. Solder is engaged between the acoustic elements and the conductive elements of the interposer such that the conductive elements of the interposer are electrically connected to the acoustic elements through the solder.

In another embodiment, an ultrasound transducer includes an array of acoustic elements, a thermal backing layer, and an interposer having conductive elements. The interposer is mechanically connected to the thermal backing layer. Solder is engaged between the acoustic elements and the conductive elements of the interposer such that the conductive elements of the interposer are electrically connected to the acoustic elements through the solder.

In another embodiment, a method is provided for manufacturing an ultrasound transducer. The method includes providing an array of acoustic elements, providing an interposer having conductive elements, arranging the acoustic elements and the interposer in a stack with at least one of an integrated circuit or a thermal backing layer; and electrically connecting the conductive elements of the interposer to the acoustic elements using solder.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and/or the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide ultrasound transducers and methods for manufacturing ultrasound transducers. An ultrasound transducer in accordance with various embodiments includes an array of acoustic elements and an interposer. The interposer includes conductive elements. Solder is engaged with the conductive elements of the interposer to electrically connect the interposer to the array of acoustic elements.

A technical effect of at least some embodiments is providing a connection between various components of an ultrasound transducer using solder, wherein the connection has a predetermined mechanical strength that facilitates preventing the connection from being severed, for example via the exposure to water and/or other liquids. A technical effect of at least some embodiments is providing a connection between various components of an ultrasound transducer using solder, wherein the connection has a faster cure time and/or superior bond strength. A technical effect of at least some embodiments is providing an ultrasound transducer that can be manufactured in less time, that is more robust to temperature changes, and/or that is more robust to being soaked in water and/or other liquids.

Figure 1:
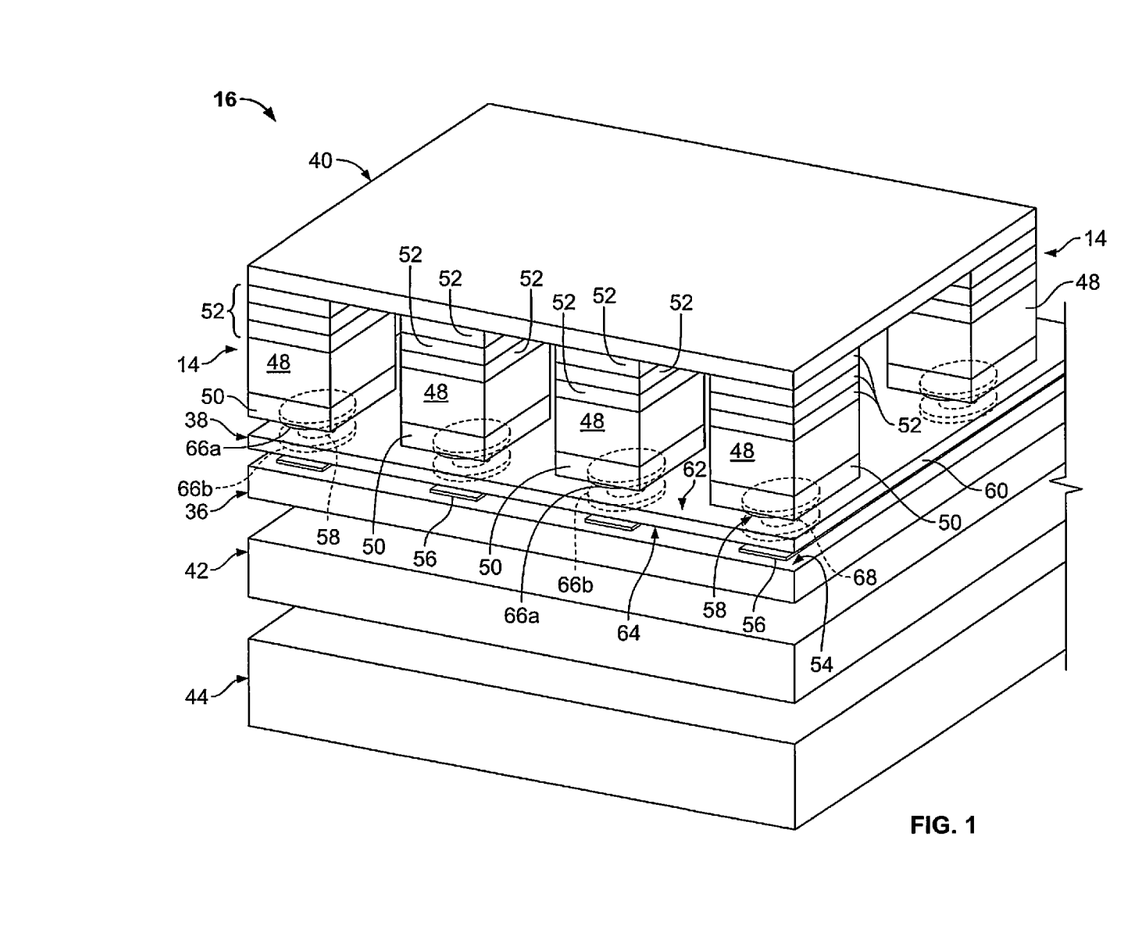
FIG. 1 is an exploded perspective view of an ultrasound transducer formed in accordance with various embodiments.
Figure 2:
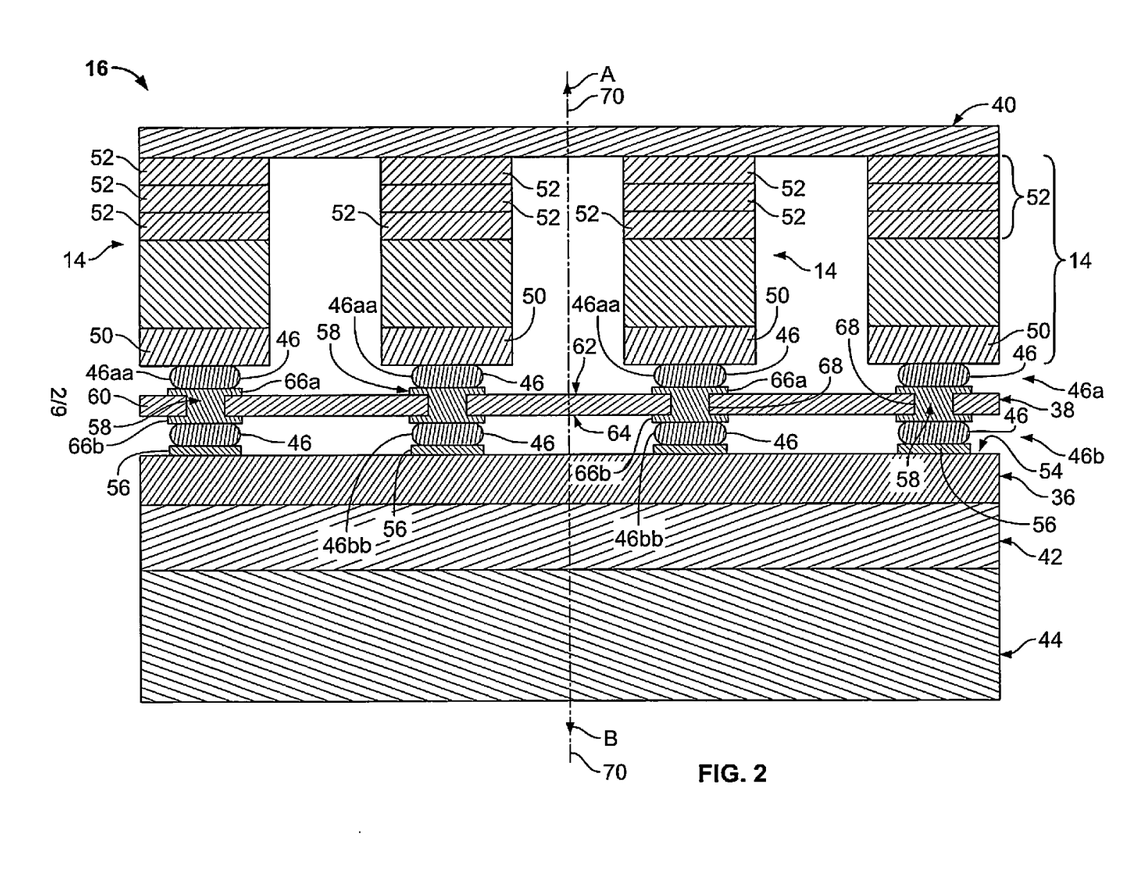
FIG. 2 is a cross-sectional view of the ultrasound transducer shown in FIG. 1.

FIG. 1 is an exploded perspective view of a portion of the ultrasound transducer 16 formed in accordance with various embodiments. FIG. 2 is an unexploded cross-sectional view of the ultrasound transducer 16. The ultrasound transducer 16 includes the array of acoustic elements 14, an integrated circuit 36, and an interposer 38 that electrically connects the acoustic elements 14 to the integrated circuit 36. The ultrasound transducer 16 may also include a lens 40, a backing 42, and/or a heat sink 44. The backing 42 may be a relatively high acoustic attenuation material to dampen backside acoustic energy. As will be described in more detail below, the interposer 38 is electrically connected to the acoustic elements 14 and/or to the integrated circuit 36 using solder 46. The solder 46 also mechanically connects the interposer 38 to the acoustic elements 14 and/or to the integrated circuit 36. The solder 46 is not shown in FIG. 1 for clarity.

In an exemplary embodiment, the lens 40, the array of acoustic elements 14, the interposer 38, the integrated circuit 36, the backing 42, and the heat sink 44 are arranged in a stack, as can be seen in FIGS. 1 and 2. Within the stack, the interposer 38 extends between the integrated circuit 36 and the acoustic elements 14. Other relative arrangements of the lens 40, the acoustic elements 14, the interposer 38, the integrated circuit 36, the backing 42, and the heat sink 44 may be provided in addition or alternative to the illustrated stack.

The acoustic elements 14 may be arranged in any number of dimensions. For example, the acoustic elements 14 may be arranged in a one dimensional (1D) array, a 1.5D array, a 1.75D array, a two-dimensional (2d) array, and/or the like. A variety of geometries may also be used.

Each acoustic element 14 includes an acoustic layer 48 that is configured to generate and transmit acoustic energy into the body or other volume and receive backscattered acoustic signals from the body or other volume to create and display an image. The acoustic layer 48 may have any value of acoustic impedance, such as, but not limited to, between approximately 3 MRayls and approximately 35 MRayls. The acoustic layer 48 may include electrodes (not shown). The acoustic layer 48 may be any type of acoustic layer that is formed from any material(s), such as, but not limited to, a piezoelectric ceramic (e.g., lead zirconate titanate (PZT), lead magnesium niobate-lead titanite (PMN-PT), and/or the like), a piezocomposite, piezoelectric crystals, a piezoelectric single crystal, a piezopolymer, and/or the like. In some embodiments, the acoustic layer 48 may include more than one sub-layer of one material or of two or more different materials. In other words, in some embodiments, the acoustic layer 48 may include multiple sub-layers of the same material, while in other embodiments the acoustic layer 48 may include multiple layers of different materials.

Each acoustic element 14 may include one or more other layers in addition to the acoustic layer 48. For example, each acoustic element 14 may include one or more matching layers (not shown), one or more conductive film layers (not shown), and/or one or more dematching layers (not shown). Each acoustic element 14 may include any number of layers overall. In an exemplary embodiment, each acoustic element 14 includes a dematching layer 50 and three matching layers 52. But, each acoustic element 14 may include any number of dematching layers 50 and may include any number of matching layers 52.

The dematching layer 50 has a relatively high acoustic impedance and functions to clamp the acoustic layer 48 so most of the acoustic energy is to transmit to the front of the transducer. However, a relatively small amount of backside acoustic energy can still be existed and reflected back to the front side that can cause artifacts in ultrasound images generated from ultrasound signals acquired by the ultrasound transducer. Therefore, the backing layer 42 is usually preferred to be a relatively high acoustic attenuation material to damp down the backside acoustic energy. The backing layer 42 may have any thickness, such as, but not limited to, between approximately 1 mm and approximately 5 mm. Consequently, a majority of the acoustic energy is reflected out a front face of the acoustic layer 48. The dematching layer 50 may have any value of acoustic impedance, such as, but not limited to, between approximately 40 MRayls and approximately 120 MRayls, between approximately 60 MRayls and approximately 100 MRayls, and/or greater than approximately 70 MRayls. In some embodiments, the dematching layer 50 has an acoustic impedance that is higher than the acoustic impedance of the acoustic layer 48. The dematching layer 50 may have relatively good thermal conductivity that can carry over, or transfer, heat generated by the acoustic layer 48 to the backside of the ultrasound transducer 16 and the heat sink 44.

The dematching layer 50 may be any type of dematching layer that is formed from any material(s), such as, but not limited to, a carbide compound material (e.g., zirconium, tungsten, silicon, titanium, tantalum carbide, and/or the like) and/or the like. The dematching layer 50 may have any thickness, which may depend on the frequency of the ultrasound transducer 16. Examples of the thickness of the dematching layer 50 include, but are not limited to, between approximately 50 um and approximately 350 um. The dematching layer 50 may be laminated to the acoustic layer 48 using any suitable method, structure, process, means, and/or the like, such as, but not limited to, using epoxy having an exemplary thickness of less than approximately 5 um.

In some embodiments, the dematching layer 50 is coated with an electrically conductive coating (not shown) of metal and/or another electrical conductor. The electrically conductive coating may facilitate electrical connection between the dematching layer 50 and the solder 46. The dematching layer 50 may be coated with the electrically conductive coating using any suitable method, structure, process, means, and/or the like. One example of forming the electrically conductive coating on the dematching layer 50 is to first sputter with Ni or Cr material as a seed layer (e.g., less than approximately 0.1 um) and then add a layer of gold (e.g., less than approximately 1 um). The layer of gold may then be electroplated or electrolysis with Ni (e.g., less than approximately 5 um) and gold (e.g., less than approximately 0.2 um) on the outside to prevent oxidation.

In some embodiments, and in addition or alternatively to the electrically conductive coating on the dematching layer 50, the acoustic elements 14 may be provided with electrical contacts (not shown) having any other structure than the electrically conductive coating. Such electrical contacts of the acoustic elements 14 may be, but are not limited to, solder pads, solder bumps, stud bumps, plated bumps, and/or the like.

The matching layers 52 facilitate matching of an impedance differential that may exist between the acoustic elements 14 and a patient. Any number of matching layers 52 may be provided. Each matching layer 52 may have any value of acoustic impedance, such as, but not limited to, between approximately 2 MRayls and approximately 15 MRayls and/or less than approximately 10 MRayls. In some embodiments, each matching layer 52 has an acoustic impedance that is less than the acoustic impedance of the acoustic layer 48. In some embodiments, a plurality of matching layers 52 are provided that provide a progressive reduction in acoustic impedance from the acoustic layer 48. For example, in some embodiments, three matching layers 52 are provided, wherein the matching layer 52 closest to the acoustic layer 48 is approximately 15 MRayls, the next matching layer 52 is approximately 8 MRayls, and the matching layer 52 farthest from the acoustic layer 48 is approximately 3 MRayls.

Each matching layer 52 may be any type of matching layer that is formed from any material(s), such as, but not limited to, filled epoxy, metal-impregnated graphite, a glass ceramic, and/or the like. Each matching layer 52 may be electrically conductive or electrically non-conductive. When a matching layer 52 is electrically non-conductive, the matching layer 52 may include a conductive film layer (not shown) thereon. One or more matching layers 52 (and/or a conductive film layer thereon) may provide an electrical ground connection for the corresponding acoustic element 14. Each matching layer 52 may have any thickness and the matching layers 52 may have any combined thickness. Examples of the combined thickness of the matching layers 52 include, but are not limited to, a thickness of approximately a quarter wavelength ($\frac{1}{4}$) $\lambda$ at the resonant frequency.

The integrated circuit 36 may be any type of integrated circuit, such as, but not limited to, an application specific integrated circuit (ASIC) and/or the like. Various components of an ultrasound system (e.g., the ultrasound system 10 shown in FIG. 5) may be included within the integrated circuit 36. In an exemplary embodiment, the integrated circuit 36 includes a transmitter 12 (shown in FIG. 5), a receiver 18 (shown in FIG. 5), and beamforming electronics 20 (shown in FIG. 5) of the ultrasound system 10.

The integrated circuit 36 includes an interposer side 54 and a plurality of electrical contacts 56 that extend along the interposer side 54. The integrated circuit 36 may include electrical traces, electrical vias, and/or other electrical circuitry that facilitates performing the operations and functions of the various components of the integrated circuit 36. The electrical contacts 56 of the integrated circuit 36 are configured to be electrically connected to corresponding conductive elements 58 of the interposer 38 to establish an electrical connection between the integrated circuit 36 and the interposer 38, as will be described below. The electrical contacts 56 are illustrated in FIGS. 1 and 2 as solder pads. But, each electrical contact 56 may additionally or alternatively include any other structure, such as, but not limited to, solder bumps, stud bumps, plated bumps, and/or the like.

The electrical contacts 56 of the integrated circuit 36 may include a plurality of different types of connections, such as, but not limited to, sensor pads, signal input/output (I/O), power, control functions, relatively high voltage connections, relatively low noise connections, and/or the like. For example, the electrical contacts 56 shown herein are sensor pads that are electrically connected to corresponding acoustic elements 14 through the interposer 38. The electrical contacts 56 of the integrated circuit 36 may further include electrical contacts (not shown) that represent other functions besides the sensor pads (such as, but not limited to, signal input/output (I/O), power, control functions, and/or the like) and that are electrically connected to the interposer 38 using the solder 46 in a substantially similar manner to that described below and illustrated herein with respect to the sensor pads.

The interposer 38 includes a substrate 60 and the conductive elements 58. The substrate 60 includes opposite sides 62 and 64. The side 62 faces the acoustic elements 14, while the side 64 faces the interposer side 54 of the integrated circuit 36. The conductive elements 58 are held by the substrate 60 and include electrical contacts 66a and 66b. The electrical contacts 66a of the conductive elements 58 extend along the side 62 of the substrate 60 for electrical connection to the acoustic elements 14. The electrical contacts 66b of the conductive elements 58 extend along the side 64 of the substrate 60 for electrical connection to the electrical contacts 56 of the integrated circuit 36. In an exemplary embodiment, the electrical contacts 66a have the same pattern and pitch as the pattern and pitch of the electrical contacts 66b. Alternatively, the electrical contacts 66a and 66b have different patterns and pitches, for example in embodiments wherein the array of acoustic elements 14 has a different pattern and/or pitch than the electrical contacts 56 of the integrated circuit 36.

In an exemplary embodiment, the conductive elements 58 are one-piece elements that include the electrical contacts 66a and 66b and an interior segment 68 that extends through the substrate 60 from the corresponding electrical contact 66a to the corresponding electrical contact 66b. In addition or alternatively, one or more of the conductive elements 58 includes an electrical via (not shown) that extends into the substrate 60, an electrical trace (not shown) that extends on the side 62, on the side 64, and/or on an internal layer (not shown) of the substrate 60, and/or other electrical circuitry. For example, in some embodiments, the electrical contacts 66a and 66b of a conductive element 58 are discrete structures that are mechanically and electrically connected together through one or more electrical traces of the interposer 38. Moreover, and for example, in some embodiments a conductive element 58 includes an electrically conductive via and the corresponding electrical contacts 66a and 66b of the conductive element 58 are solder pads of the electrically conductive via. The electrical contacts 66a and 66b may each be any type of electrical contact having any structure, such as, but not limited to, solder pads (as is illustrated herein), solder bumps, stud bumps, plated bumps, and/or the like. The conductive elements 58 may each be fabricated from any material(s), such as, but not limited to, a metal, an electrically conductive epoxy, silver epoxy, and/or the like. Although the electrical contacts 66a and 66b are each shown as extending outwardly on the respective sides 62 and 64, each electrical contact 66a and 66b may alternatively be flush with, or recessed relative to, the respective side 62 and 64.

The substrate 60 of the interposer 38 may be fabricated from any material(s). Examples of materials of the substrate 60 include, but are not limited to, a relatively low acoustic impedance material (e.g., an acoustic impedance of less than approximately 10 MRayls), an organic material, a polyimide (e.g., Kapton®), and/or the like. The substrate 60 is shown as including only a single layer, but the substrate 60 may include any number of layers. In some embodiments, the substrate 60 is generally flexible such that the interposer 38 is a flexible circuit (sometimes referred to as a "flex circuit"). The interposer 38 may have an acoustic impedance, such as, but not limited to less than approximately 10 MRayls and/or between approximately 2 MRayls and approximately 15 approximately 15 MRayls.

Figure 5:
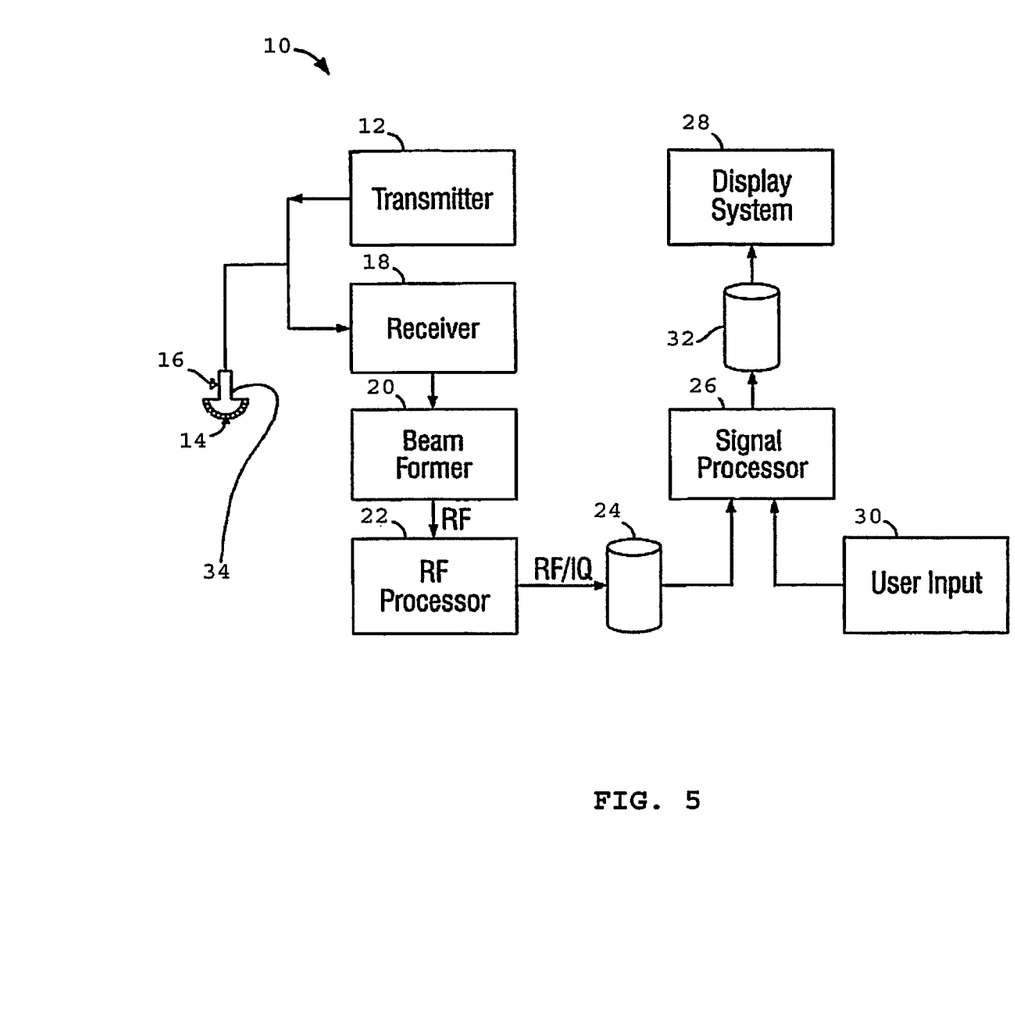
FIG. 5 is a block diagram of an ultrasound system in which various embodiments may be implemented.

In some embodiments, the interposer 38 is a cable that electrically connects the ultrasound transducer 16 to other components of an ultrasound system (e.g., the ultrasound system 10 shown in FIG. 5). For example, the interposer 38 may be a cable that provides signal, ground, control, and/or power connections between the ultrasound transducer 16 and an RF processor 22 (shown in FIG. 5), a memory 24 (shown in FIG. 5), a signal processor 26 (shown in FIG. 5), a user input 30 (shown in FIG. 5), a memory 32 (shown in FIG. 5), and/or a display system 28 (shown in FIG. 5). In some embodiments wherein the interposer 38 is a cable and a flexible circuit, the interposer 38 is a flat flexible cable, which is sometimes referred to as a "flat flex circuit", a "flat flexible conductor cable", a "flex cable", a "cable flex circuit", and/or a "flexible flat cable".

Referring now solely to FIG. 2, in an exemplary embodiment, the interposer 38 is electrically connected to both the array of acoustic elements 14 and the integrated circuit 36 using the solder 46. More specifically, a layer 46a of the solder 46 is engaged with both the conductive elements 58 of the interposer 38 and the dematching layers 50 of the acoustic elements 14. Accordingly, the interposer 38 and the array of acoustic elements 14 are electrically connected together through the layer 46a of the solder 46. Similarly, a layer 46b of the solder 46 is engaged with both the conductive elements 58 of the interposer 38 and the electrical contacts 56 of the integrated circuit 36. Accordingly, the interposer 38 and the integrated circuit 36 are electrically connected together through the layer 46b of the solder 46. The interposer 38 thus electrically connects the array of acoustic elements 14 to the integrated circuit 36. Because the electrical contacts 56 of the integrated circuit 36 may include a plurality of different types of connections (e.g., relatively high voltage connections and relatively low noise connections), the solder layer 46b may be used to electrically connect a plurality of different types of connections of the integrated circuit 36 to the interposer 38. The layer 46a of the solder 46 may be referred to herein as a "first solder layer", while the layer 46b of the solder 46 may be referred to herein as a "second solder layer".

As can be seen in FIG. 2, each layer 46a and 46b of the solder 46 includes a plurality of individual solder elements 46aa and 46bb. Referring first to the layer 46a of the solder 46 that extends between the acoustic elements 14 and the interposer 38, each individual solder element 46aa is engaged between one or more corresponding electrical contacts 66a of the interposer 38 and the dematching layer 50 of one or more corresponding acoustic elements 14. In other words, each individual solder element 46aa is engaged, in electrical connection, with the corresponding electrical contact(s) 66a and with the corresponding dematching layer(s) 50. In embodiments wherein the electrically conductive coating is included on the dematching layers 50, the solder elements 46aa engage the electrically conductive coating of the corresponding dematching layer(s) 50. Each individual solder element 46aa provides an electrical path, along a conduction axis 70, between the corresponding electrical contact(s) 66a of the interposer 38 and the corresponding acoustic element(s) 14. Accordingly, the electrical contacts 66a of the interposer 38 are electrically connected to the acoustic elements 14 through the individual solder elements 46aa of the layer 46a of the solder 46. The individual solder elements 46aa conduct electrical energy along the conduction axis 70 in both of the directions A and B. Accordingly, the solder layer 46a is configured to conduct both the transmission and reception of signals.

The layer 46a of the solder 46 may include any number of individual solder elements 46aa for any number of electrical contacts 66a and for any number of acoustic elements 14. For example, each individual solder element 46aa may be engaged with any number of acoustic elements 14 and with any number of electrical contacts 66a, whether or not the number of acoustic elements 14 engaged by the individual solder element 46aa is the same as the number of electrical contacts 66a engaged by the individual solder element 46aa. In some embodiments, each individual solder element 46aa is engaged with at least two acoustic elements 14. Each individual solder element 46aa may have any thickness along the conduction axis 70, such as, but not limited to, less than approximately 75 um and/or less than approximately 25 um.

Referring now to the layer 46b of the solder 46 that extends between the interposer 38 and the integrated circuit 36, each individual solder element 46bb is engaged between one or more corresponding electrical contacts 66b of the interposer 38 and one or more corresponding electrical contacts 56 of the integrated circuit 36. In other words, each individual solder element 46bb is engaged, in electrical connection, with the corresponding electrical contact(s) 66b and with the corresponding electrical contact(s) 56. Each individual solder element 46bb provides an electrical path, along the conduction axis 70, between the corresponding electrical contact(s) 66b of the interposer 38 and the corresponding electrical contact(s) 56. Accordingly, the electrical contacts 66b of the interposer 38 are electrically connected to the integrated circuit 36 through the individual solder elements 46bb of the layer 46b of the solder 46. The individual solder elements 46bb conduct electrical energy along the conduction axis 70 in both of the directions A and B. Accordingly, the solder layer 46b is configured to conduct both the transmission and reception of signals.

The layer 46b of the solder 46 may include any number of individual solder elements 46bb for any number of electrical contacts 66b and for any number of electrical contacts 56. For example, each individual solder element 46bb may be engaged with any number of electrical contacts 56 and with any number of electrical contacts 66b, whether or not the number of electrical contacts 56 engaged by the individual solder element 46bb is the same as the number of electrical contacts 66b engaged by the individual solder element 46bb. Each individual solder element 46bb may have any thickness along the conduction axis 70, such as, but not limited to, less than approximately 50 um and/or less than approximately 25 um. When the solder is cured under a confined environment such as appropriate pressure and temperature, the thickness may need to be controlled uniformly and must be thin enough so that the impact on the ultrasound signal path will be minimized. The soldering and assembling steps can be processed such as, but not limited to, by industrial standard equipment, for example pick and place equipment used in the semiconductor industry.

The layers 46a and 46b of the solder 46 provide a mechanical connection between the interposer 38 and the acoustic elements 14 and between the interposer 38 and the integrated circuit 36, respectively. In some embodiments, an adhesive (not shown) extends between the substrate 60 of the interposer 38 and the acoustic elements 14 to provide a mechanical connection between the substrate 60 and the acoustic elements 14 (in addition to the mechanical connection between the electrical contacts 66a and the acoustic elements 14 provided by the solder layer 46a). Moreover, in some embodiments, an adhesive (not shown) extends between the substrate 60 of the interposer 38 and the integrated circuit 36 to provide a mechanical connection between the substrate 60 and the integrated circuit 36 (in addition to the mechanical connection between the electrical contacts 66a and the electrical contacts 56 provided by the solder layer 46b). In addition or alternative to the adhesive, in some embodiments any other structure, fastener, means, and/or the like may be used to mechanically connect the interposer 38 to the array of acoustic elements 14 and/or to the integrated circuit 36.

In alternative to the solder layer 46b, the electrical contacts 56 of the integrated circuit 36 may be electrically connected to the electrical contacts 66b of the interposer 38 using an electrically conductive adhesive (not shown) that is anisotropically conductive. In other words, in some embodiments, the ultrasound transducer 16 does not include the layer 46b of the solder 46. By "anisotropically conductive", it is meant that the electrically conductive adhesive conducts electrical energy along at least the conduction axis 70, but does not conduct electrical energy along at least one other axis that is oriented at a non-zero angle relative to the conduction axis 70.

Figure 3:
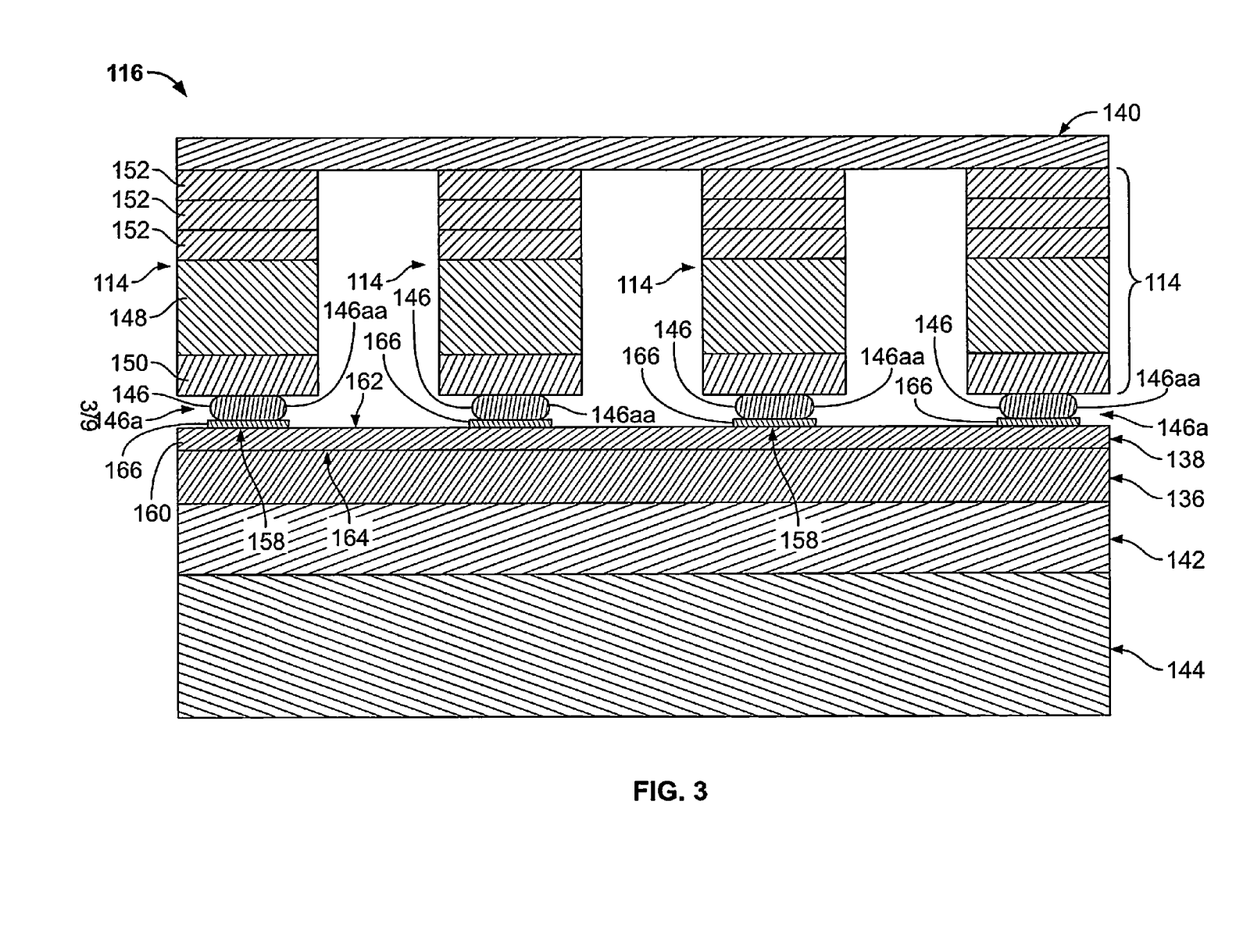
FIG. 3 is a cross-sectional view of another ultrasound transducer formed in accordance with various embodiments.

FIG. 3 is a cross-sectional view of another ultrasound transducer 116 formed in accordance with various embodiments. FIG. 3 illustrates an embodiment wherein the ultrasound transducer 116 includes a thermal backing layer 136. The ultrasound transducer 116 includes an array of acoustic elements 114, an interposer 138, and the thermal backing layer 136. The ultrasound transducer 116 may also include a lens 140, a backing 142, and/or a heat sink 144. As will be described in more detail below, the interposer 138 is electrically connected to the acoustic elements 114 using solder 146. The solder 146 also mechanically connects the interposer 138 to the acoustic elements 114.

In an exemplary embodiment, the lens 140, the array of acoustic elements 114, the interposer 138, the thermal backing layer 136, the backing 142, and the heat sink 144 are arranged in a stack, as can be seen in FIG. 3. Within the stack, the interposer 138 extends between the thermal backing layer 136 and the acoustic elements 114. Other relative arrangements of the lens 140, the acoustic elements 114, the interposer 138, the thermal backing layer 136, the backing 142, and the heat sink 144 may be provided in addition or alternative to the illustrated stack.

The acoustic elements 114 may be arranged in any number of dimensions. For example, the acoustic elements 114 may be arranged in a one dimensional (1D) array, a 1.5D array, a 1.75D array, a two-dimensional (2d) array, and/or the like. A variety of geometries may also be used. In an exemplary embodiment, each acoustic element 114 includes an acoustic layer 148, a dematching layer 150, and three matching layers 152. But, each acoustic element 114 may include any number of dematching layers 150 and may include any number of matching layers 152. The interposer 138 is used as an electrical connection to the specific geometry formed by individual acoustic elements 114 to the outside channels through a multi-channel cable. The acoustic elements 114 of the ultrasound transducer are connected to the system using the multi-channel cable.

The interposer 138 includes a substrate 160 and conductive elements 158. The substrate 160 includes opposite sides 162 and 164. The thermal backing layer 136 is mechanically connected to the interposer 138 on the side 164 of the interposer 138, as can be seen in FIG. 3. The conductive elements 158 are held by the substrate 160 and include electrical contacts 166. The electrical contacts 166 of the conductive elements 158 extend along the side 162 of the substrate 160 for electrical connection to the acoustic elements 114. In some embodiments, the substrate 160 is generally flexible such that the interposer 138 is a flexible circuit (sometimes referred to as a "flex circuit"). Moreover, in some embodiments, the interposer 138 is a cable that electrically connects the ultrasound transducer 116 to other components of an ultrasound system (e.g., the ultrasound system 10 shown in FIG. 5). In some embodiments wherein the interposer 138 is a cable and a flexible circuit, the interposer 138 is a flat flexible cable, which is sometimes referred to as a "flat flex circuit", a "flat flexible conductor cable", a "flex cable", a "cable flex circuit", and/or a "flexible flat cable".

As briefly described above, the interposer 138 is electrically connected to the array of acoustic elements 114 using the solder 146. Specifically, a layer 146a of the solder 146 is engaged with both the conductive elements 158 of the interposer 138 and the dematching layers 150 of the acoustic elements 114. The layer 146a of the solder 146 includes a plurality of individual solder elements 146aa. Each individual solder element 146aa is engaged between one or more corresponding electrical contacts 166 of the interposer 138 and the dematching layer 150 of one or more corresponding acoustic elements 114. In other words, each individual solder element 146aa is engaged, in electrical connection, with the corresponding electrical contact(s) 166 and with the corresponding dematching layer(s) 150. In embodiments wherein an electrically conductive coating is included on the dematching layers 150, the solder elements 146aa engage the electrically conductive coating of the corresponding dematching layer(s) 150. Each individual solder element 146aa provides an electrical path between the corresponding electrical contact(s) 166 of the interposer 138 and the corresponding acoustic element(s) 114. Accordingly, the electrical contacts 166 of the interposer 138 are electrically connected to the acoustic elements 114 through the individual solder elements 146aa of the layer 146a of the solder 146. The solder layer 146a is configured to conduct both the transmission and reception of signals.

Figure 4:
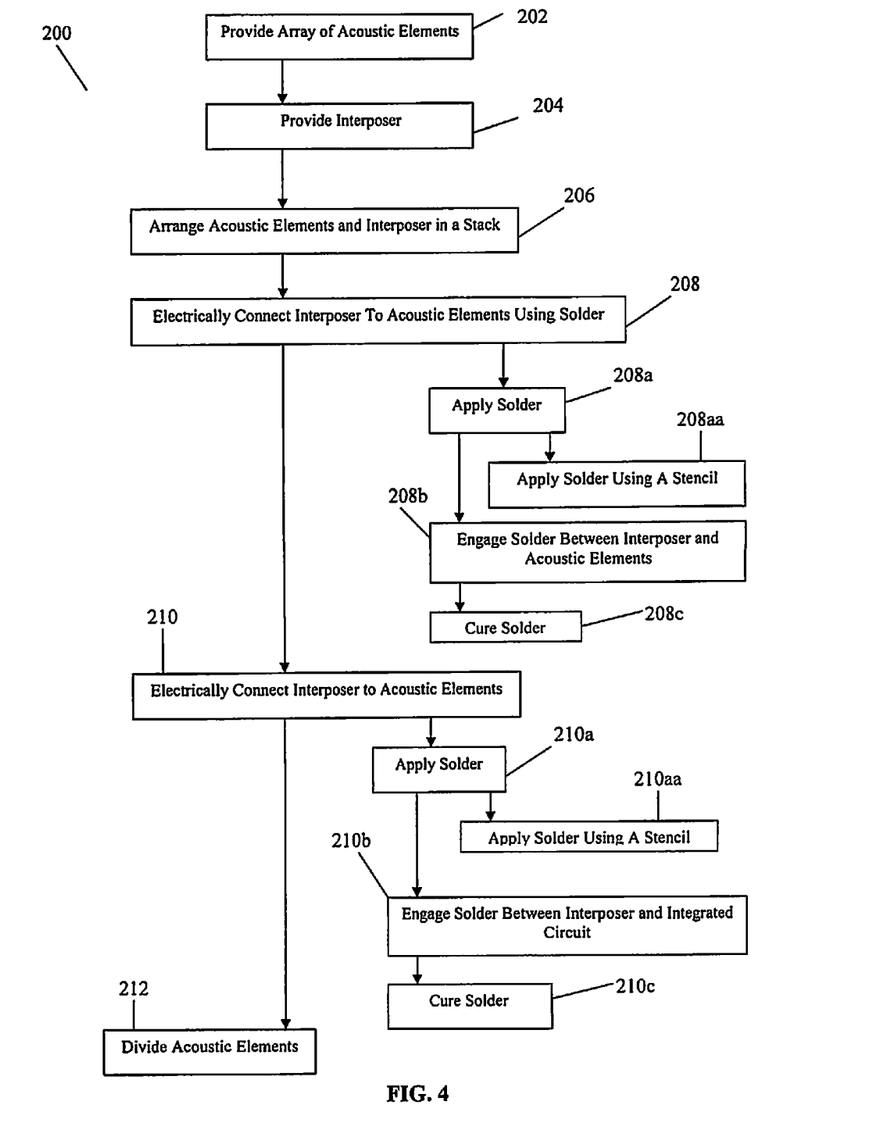
FIG. 4 is a flowchart illustrating a method for manufacturing an ultrasound transducer in accordance with various embodiments.

FIG. 4 is a flowchart illustrating a method 200 for manufacturing an ultrasound transducer in accordance with various embodiments. Exemplary uses of the method 200 include manufacturing the ultrasound transducer 16 shown in FIGS. 1, 2, and 5 or the ultrasound transducer 116 shown in FIG. 3. The method 200 includes, at 202, providing an array of acoustic elements (e.g., the acoustic elements 14 shown in FIGS. 1, 2, and 5 or the acoustic elements 114 shown in FIG. 3). In some embodiments, the acoustic elements are provided, at 202, as a single continuous member (e.g., a single continuous sheet). In other embodiments, the acoustic elements are provided, at 202, as a plurality of separate individual acoustic elements or as a plurality of separate groups of acoustic elements.

At 204, the method 200 includes providing an interposer (e.g., the interposer 38 shown in FIGS. 1 and 2 or the interposer 138 shown in FIG. 3), wherein the interposer includes a plurality of conductive elements (e.g., the conductive elements 58 shown in FIGS. 1 and 2 or the conductive elements 158 shown in FIG. 3). The method 200 may include arranging, at 206, the array of acoustic elements and the interposer in a stack with an integrated circuit (e.g., the integrated circuit 26 shown in FIGS. 1 and 2) and/or a thermal backing layer (e.g., the thermal backing layer 136 shown in FIG. 3). The interposer may include a side that faces the array of acoustic elements and a side that faces the integrated circuit and/or the thermal backing layer, wherein the sides may be the same side or opposite sides. For example, when arranged within a stack with the array of acoustic elements and the integrated circuit and/or the thermal backing layer, the interposer has a side that faces the array of acoustic elements and an opposite side that faces the integrated circuit and/or thermal backing layer. Moreover, and for example, when the interposer is not arranged within a stack, the same side of the interposer may face the array of acoustic elements and the integrated circuit and/or thermal backing layer or different sides of the interposer may face the array of acoustic elements and the integrated circuit and/or thermal backing layer.

At 208, the method 200 includes electrically connecting the conductive elements of the interposer to the array of acoustic elements using solder (e.g., the solder 46 shown in FIG. 2 or the solder 146 shown in FIG. 3). Electrically connecting the interposer to the array of acoustic elements at 208 may include applying, at 208a, the solder to the acoustic elements and/or to the conductive elements of the interposer. In some embodiments, applying at 208a the solder to the acoustic elements and/or the conductive elements includes applying, at 208aa, the solder to the acoustic elements and/or the conductive elements using a stencil (not shown), as will be described in more detail below.

At 208b, the method 200 includes engaging the solder between the conductive elements of the interposer and the acoustic elements such that the acoustic elements are electrically connected to the conductive elements of the interposer through the solder. At 208c, the method step 208 includes curing the solder using a reflow process. Once cured, the solder provides both a mechanical and an electrical connection between the interposer and the acoustic elements. The step 208 may be performed using any soldering process, equipment, and/or the like, such as, but not limited to, using pick and place automation equipment, using semiconductor bumping technology, and/or the like.

In some embodiments, the ultrasound transducer manufactured in accordance with the method 200 includes an integrated circuit. For example, as described above, the method 200 may include arranging, at 206, the array of acoustic elements and the interposer in a stack with an integrated circuit. At 210, the method 200 may include electrically connecting the conductive elements of the interposer to the integrated circuit using solder (e.g., the solder 46 shown in FIG. 2). Electrically connecting the interposer to the integrated circuit at 210 may include applying, at 210a, the solder to electrical contacts (e.g., the electrical contacts 56 shown in FIGS. 1 and 2) of the integrated circuit and/or to the conductive elements of the interposer. In some embodiments, applying at 210a the solder to the electrical contacts and/or the conductive elements includes applying, at 210aa, the solder to the electrical contacts and/or the conductive elements using a stencil (not shown), as will be described in more detail below.

At 210b, the method 200 may include engaging the solder between the conductive elements of the interposer and the electrical contacts of the integrated circuit such that the electrical contacts of the integrated circuit are electrically connected to the conductive elements of the interposer through the solder. At 210c, the method step 210 may include curing the solder using a reflow process. Once cured, the solder provides both a mechanical and an electrical connection between the interposer and the integrated circuit. The step 210 may be performed using any soldering process, equipment, and/or the like, such as, but not limited to, using pick and place automation equipment, using semiconductor bumping technology, and/or the like.

As described above with respect to the integrated circuit 36 shown in FIGS. 1 and 2, the electrical contacts of the integrated circuit may include a plurality of different types of connections, such as, but not limited to, sensor pads, signal input/output (I/O), power, control functions, relatively high voltage connections, relatively low noise connections, and/or the like. In such embodiments, the step 210 of electrically connecting the conductive elements of the interposer to the integrated circuit may include electrically connecting a plurality of different types of connections of the integrated circuit to the interposer in a single operation (e.g., a single cure and pressure cycle), which may reduce a cost, time, difficulty, and/or complexity of manufacturing the ultrasound transducer. Moreover, electrically connecting the plurality of different types of connections of the integrated circuit to the interposer in a single operation may enable the electrical contacts of the integrated circuit to be more closely spaced, which may provide the integrated circuit and/or the interposer with a smaller footprint.

In embodiments wherein the acoustic elements are provided, at 202, as a single continuous member, the method 200 may include, at 212, dividing the single continuous member of the acoustic elements into a plurality of separate individual acoustic elements or into two or more separate groups of acoustic elements. In such embodiments, the step 208 of electrically connecting the conductive elements of the interposer to the array of acoustic elements may be performed in a single operation (e.g., a single cure and pressure cycle), which may reduce a cost, time, difficulty, and/or complexity of manufacturing the ultrasound transducer. In embodiments wherein the acoustic elements are provided, at 202, as a plurality of separate individual acoustic elements or two or more separate groups of acoustic elements, each individual acoustic element or group of acoustic elements may be electrically connected to the interposer in a different operation of step 208 or in a single operation of step 208.

As described above, the method 200 may include the step 208aa and/or the step 210aa of applying solder using a stencil. For example, the solder may be applied through the stencil using print screen technology. The stencil includes a plurality of openings for receiving individual solder elements (e.g., the individual solder elements 46aa shown in FIG. 2, the individual solder elements 46bb shown in FIG. 2, or the individual solder elements 146aa shown in FIG. 3) therein. The stencil may include any number of openings for any number of conductive elements of the interposer, for any number of acoustic elements, and for any number of electrical contacts of the integrated circuit. For example, each opening may receive an individual solder element that engages with any number of acoustic elements 14, with any number of conductive elements of the interposer, and/or with any number of electrical contacts of the integrated circuit. In some embodiments, each opening of the stencil receives an individual solder element that engages at least two acoustic elements. In an exemplary embodiment, each opening of the stencil receives an individual solder element that engages four acoustic elements.

The stencil may have any thickness, such as, but not limited to, less than approximately 75 um and/or less than approximately 25 um. The thickness of the stencil may be selected to provide the individual solder elements with a thickness that provides a predetermined bonding strength, that reduces or eliminates a gap between the interposer and the acoustic elements and/or between the interposer and the integrated circuit, and/or that reduces or eliminates acoustic reflection and thereby reduces or eliminates artifacts in ultrasound images generated from ultrasound signals acquired by the ultrasound transducer.

Although the method steps 210 and 212 are shown herein, and described above, as being performed after the method step 208, alternatively the step 210 and/or the step 212 is performed before, or simultaneously with, the step 208.

FIG. 5 is a block diagram of an ultrasound system 10 in which various embodiments may be implemented. The ultrasound system 10 may be used, for example, to acquire ultrasound data and generate ultrasound images. The ultrasound system 10 includes a transmitter 12 that drives the array of acoustic elements 14 (i.e., transducer elements) within or formed as part of the ultrasound transducer 16 to emit pulsed ultrasonic signals into a body or other volume. The ultrasonic signals are back-scattered from density interfaces and/or structures in the body or other volume (e.g., blood cells, fatty tissue, and/or muscular tissue in a body) to produce echoes that return to the acoustic elements 14. The echoes are received by a receiver 18. The received echoes are passed through beamforming electronics 20, which performs beamforming and outputs an RF signal. The RF signal then passes through an RF processor 22. The RF processor 22 may include a complex demodulator (not shown) that demodulates the RF signal to form IQ data pairs representative of the echo signals. The RF or IQ signal data may then be routed directly to a memory 24 for storage (e.g., temporary storage).

The ultrasound system 10 also includes a signal processor 26 to process the acquired ultrasound information (e.g., RF signal data or IQ data pairs) and prepare frames of ultrasound information for display on a display system 28. The signal processor 26 is adapted to perform one or more processing operations according to a plurality of selectable ultrasound modalities on the acquired ultrasound information. Acquired ultrasound information may be processed and/or displayed in real-time during a scanning session as the echo signals are received. Additionally or alternatively, the ultrasound ultrasound information may be stored temporarily in the memory 24 during a scanning session and then processed and/or displayed in less than real-time in a live or off-line operation.

The signal processor 26 is connected to a user input device 30 that may control operation of the ultrasound system 10. The user input device 30 may be any suitable device and/or user interface for receiving user inputs to control, for example, the type of scan or type of transducer to be used in a scan. The display system 28 includes one or more monitors that present patient information, including diagnostic ultrasound images to the user for diagnosis and/or analysis. The ultrasound system 10 may include a memory 32 for storing processed frames of acquired ultrasound information that are not scheduled to be displayed immediately. One or both of the memory 24 and the memory 32 may store three-dimensional (3D) data sets of the ultrasound data, where such 3D datasets are accessed to present 2D and/or 3D images. Multiple consecutive 3D datasets may also be acquired and stored over time, such as to provide real-time 3D or 4D display. The images may be modified and/or the display settings of the display system 28 may be manually adjusted using the user input device 30.

In addition to the acoustic elements 14, various other components of the ultrasound system 10 may be considered to be a component of the ultrasound transducer 16. For example, the transmitter 12, the receiver 18, and/or the beamforming electronics 20 may each be a component of the ultrasound transducer 16. In some embodiments, two or more components of the ultrasound system 10 are integrated into an integrated circuit (e.g., the integrated circuit 36 shown in FIGS. 1 and 2), which may be a component of the ultrasound transducer 16. For example, the transmitter 12, the receiver 18, and/or the beamforming electronics 20 may be integrated into an integrated circuit.

The ultrasound system 10 may include an ultrasound probe 34 that holds one or more various components of the ultrasound transducer 16. For example, as shown in FIG. 5, the ultrasound probe 34 holds the array of acoustic elements 14. In addition to the acoustic elements 14, and for example, the ultrasound probe 34 may hold the transmitter 12, the receiver 18, the beamforming electronics 20, and/or one or more integrated circuits that include any of the components 12, 18, and/or 20.

Figure 6:
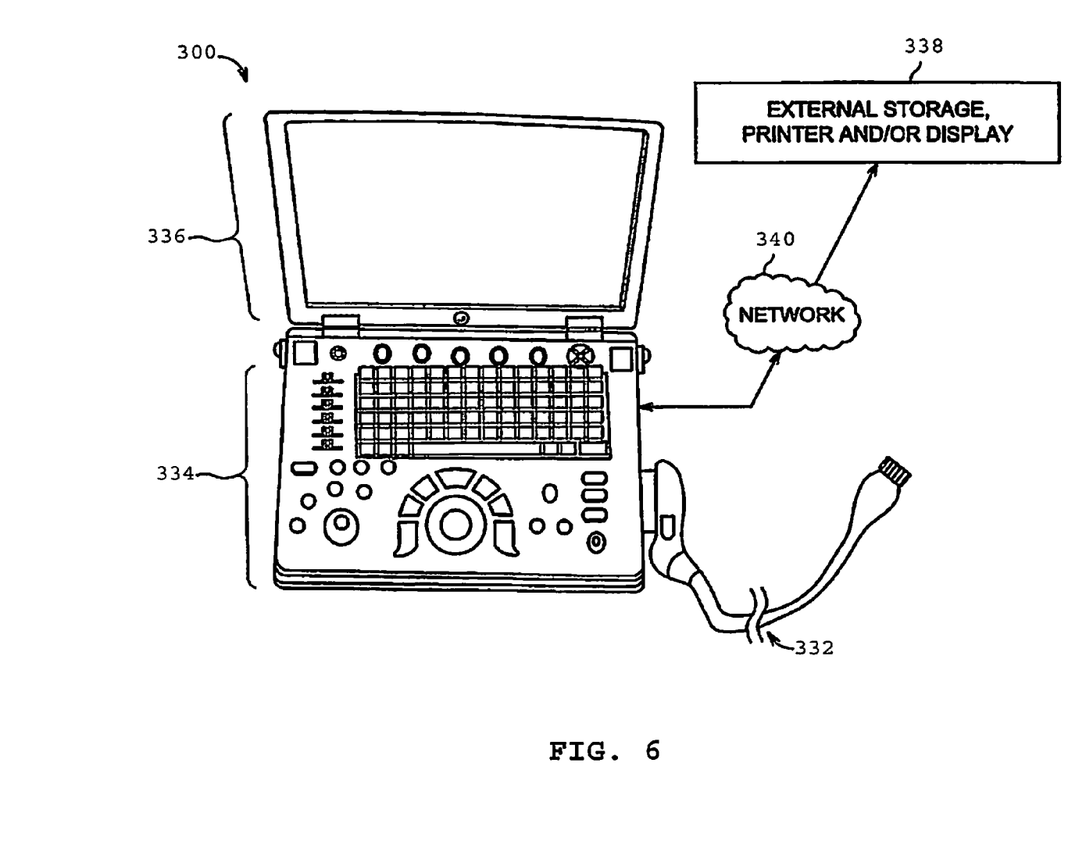
FIG. 6 is a diagram illustrating a three-dimensional (3D) capable miniaturized ultrasound system in which various embodiments may be implemented.
Figure 7:
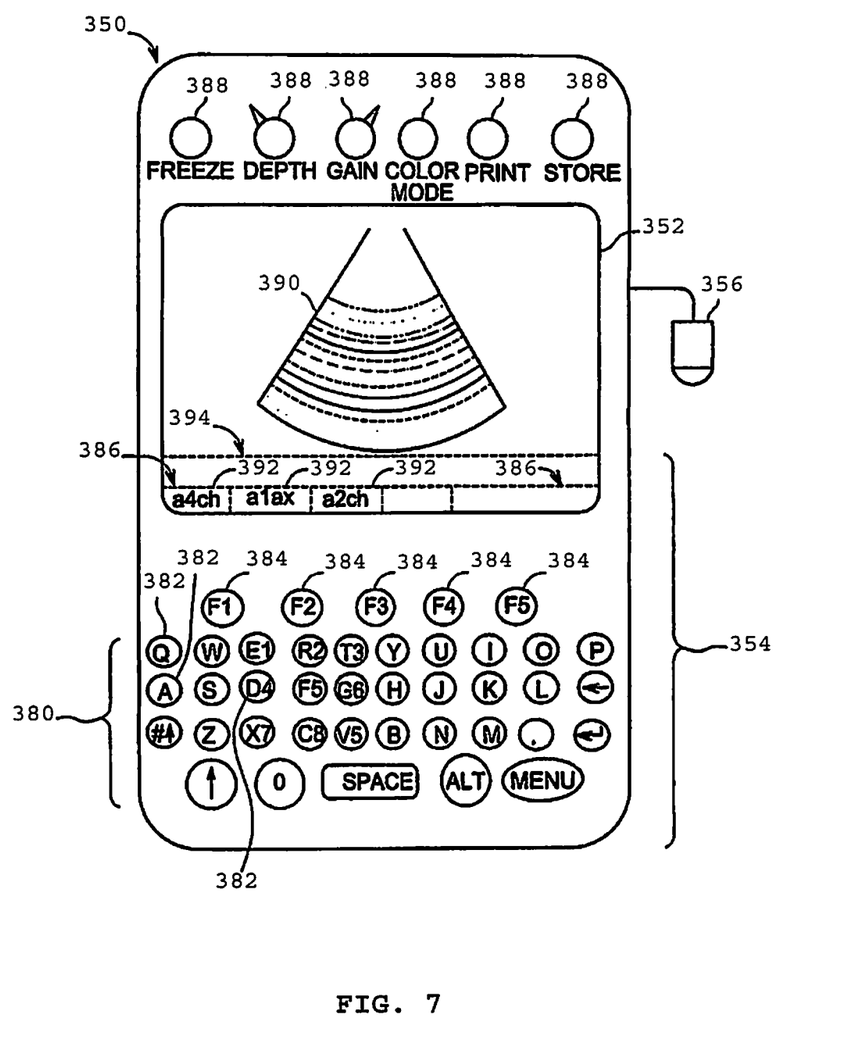
FIG. 7 is a diagram illustrating a 3D capable hand carried or pocket-sized ultrasound imaging system in which various embodiments may be implemented.
Figure 8:
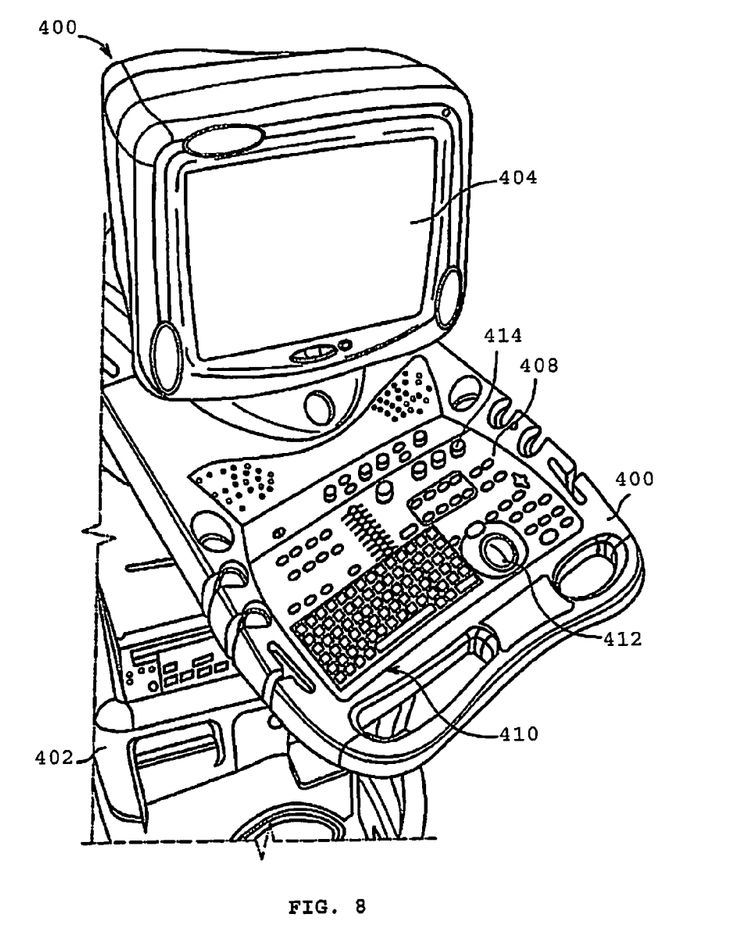
FIG. 8 is a diagram illustrating a 3D capable console type ultrasound imaging system in which various embodiments may be implemented.

The ultrasound system 10 may be embodied in a small-sized system, such as, but not limited to, a laptop computer or pocket sized system as well as in a larger console-type system. FIGS. 6 and 7 illustrate small-sized systems, while FIG. 8 illustrates a larger system.

FIG. 6 illustrates a 3D-capable miniaturized ultrasound system 300 having an ultrasound transducer 332 that may be configured to acquire 3D ultrasonic data or multi-plane ultrasonic data. For example, the ultrasound transducer 332 may have a 2D array of acoustic elements as discussed previously with respect to the ultrasound transducer 16 of FIGS. 1, 2, and 5. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 7 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, and an ultrasound transducer 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 10 (shown in FIG. 5)

FIG. 8 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and/or the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

Figure 9:
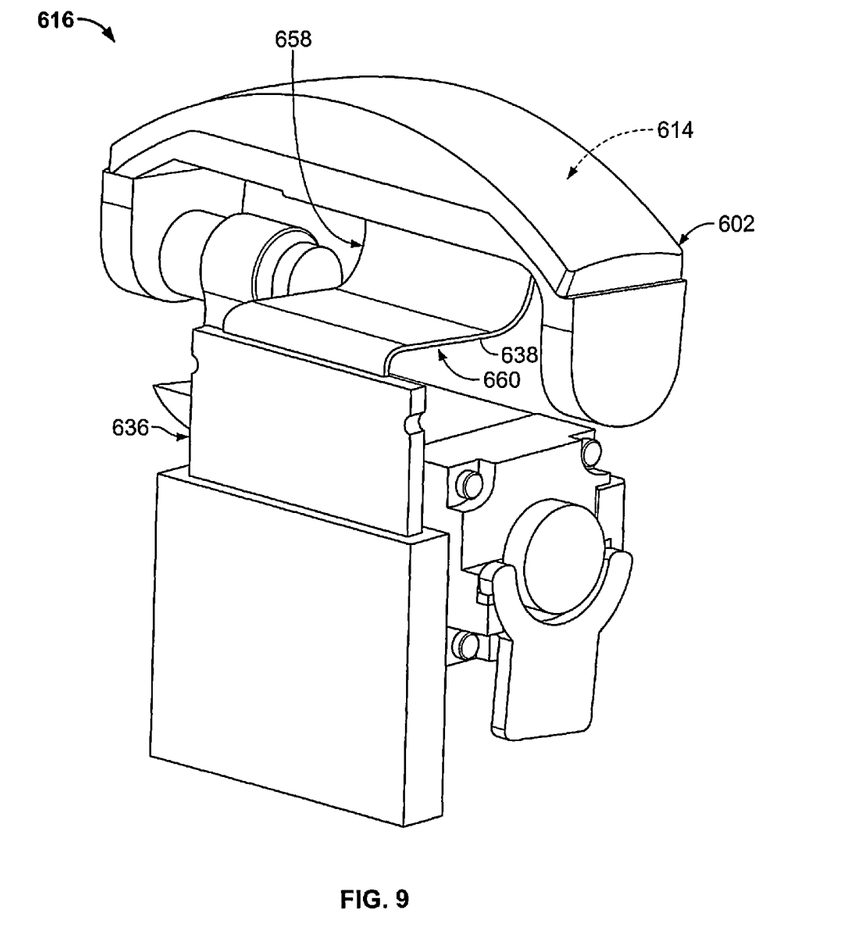
FIG. 9 is a perspective view of a portion of another ultrasound transducer formed in accordance with various embodiments.

FIG. 9 is a perspective view of a portion of another ultrasound transducer 616 formed in accordance with various embodiments. As described above, the ultrasound transducer embodiments described and/or illustrated herein are not limited to the stacked arrangement of the integrated circuit 36 (shown in FIGS. 1 and 2), the interposer 38 (shown in FIGS. 1 and 2), and the array of acoustic elements 14 (shown in FIGS. 1, 2, and 5). FIG. 9 illustrates another embodiment of an ultrasound transducer 616 having an integrated circuit 636, an interposer 638, and an array of acoustic elements 614 that are not arranged in a stack.

The ultrasound transducer 616 includes a scan head 602 and one or more integrated circuits 636. The scan head 602 includes the array of acoustic elements 614. The integrated circuit 636 is located remote from the scan head 602 such that the integrated circuit 636 is not arranged within a stack with the array of acoustic elements 614. The integrated circuit 636 is electrically connected to the array of acoustic elements 614 via the interposer 638. The interposer 638 is a flex circuit that extends from a length from the scan head 602 to the integrated circuit 636. As can be seen in FIG. 9, the interposer 638 is bent at multiple locations along the length of the interposer 638. The interposer 638 includes opposite sides 658 and 660.

The interposer 638 is electrically connected to the array of acoustic elements 614 and/or the integrated circuit 636 using solder (not shown). The interposer 638 may be electrically connected to the array of acoustic elements 614 using solder in a manner substantially similar to that described and illustrated herein with respect to the connection between the interposer 38 and the array of acoustic elements 14 using the solder 46 (shown in FIG. 2). The interposer 638 may be electrically connected to the integrated circuit 636 using solder in a manner substantially similar to that described and illustrated herein with respect to the connection between the interposer 38 and the integrated circuit 36 using the solder 46.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound transducer comprising:
   an array of acoustic elements, wherein the acoustic elements include dematching layers coated with an electrically conductive coating;
   an integrated circuit;
   an interposer comprising conductive elements for electrically connecting the acoustic elements to the integrated circuit, the conductive elements being electrically connected to the integrated circuit; and
   solder that is engaged between the acoustic elements and the conductive elements of the interposer, wherein the electrical conductive coating facilitates an electrical connection between the dematching layers and the solder such that the conductive elements of the interposer are electrically connected to the acoustic elements through the solder.

2. The ultrasound transducer of claim 1, wherein the solder is a first solder layer, the ultrasound transducer further comprising a second solder layer that is engaged between the integrated circuit and the conductive elements of the interposer such that the conductive elements of the interposer are electrically connected to the integrated circuit through the solder.

3. The ultrasound transducer of claim 1, wherein the interposer comprises at least one of a flex circuit or a flex cable.

4. The ultrasound transducer of claim 1, wherein the array of acoustic elements is one of a one-dimensional (1D) array, a 1.5D array, a 1.75D array, or a two-dimensional (2D) array.

5. The ultrasound transducer of claim 1, wherein the solder comprises individual solder elements, each individual solder element being engaged with at least two acoustic elements of the array of acoustic elements.

6. The ultrasound transducer of claim 1, wherein the array of acoustic elements, the interposer, and the integrated circuit are arranged in a stack, the interposer extending between the integrated circuit and the array of acoustic elements within the stack.

7. The ultrasound transducer of claim 1, wherein the solder is configured to conduct both the transmission and reception of signals.

8. The ultrasound transducer of claim 1, wherein the conductive elements of the interposer comprise at least one of an electrical via, an electrical trace, or an electrical contact pad.

9. The ultrasound transducer of claim 1, wherein the solder is a first solder layer and the integrated circuit comprises electrical contacts, the ultrasound transducer further comprising a second solder layer that is engaged between the conductive elements of the interposer and the electrical contacts of the integrated circuit such that the electrical contacts of the integrated circuit are electrically connected to the conductive elements of the interposer through the second solder layer.

10. An ultrasound transducer comprising:
    an array of acoustic elements, wherein the acoustic elements include dematching layers coated with an electrically conductive coating;
    a thermal backing layer;
    an interposer comprising conductive elements, the interposer being mechanically connected to the thermal backing layer; and
    solder that is engaged between the acoustic elements and the conductive elements of the interposer, wherein the electrical conductive coating facilitates an electrical connection between the dematching layers and the solder such that the conductive elements of the interposer are electrically connected to the acoustic elements through the solder.

11. The ultrasound transducer of claim 10, wherein the interposer comprises at least one of a flex circuit or a flex cable.

12. The ultrasound transducer of claim 10, wherein the array of acoustic elements is one of a one-dimensional (1D) array, a 1.5D array, a 1.75D array, or a two-dimensional (2D) array.

13. A method for manufacturing an ultrasound transducer, the method comprising:
    providing an array of acoustic elements, wherein the acoustic elements include dematching layers coated with an electrically conductive coating;
    providing an interposer having conductive elements;
    arranging the acoustic elements and the interposer in a stack with at least one of an integrated circuit or a thermal backing layer; and electrically connecting the conductive elements of the interposer to the acoustic elements using solder, wherein the electrical conductive coating facilitates an electrical connection between the acoustic elements and the solder.

14. The method of claim 13, wherein providing an interposer comprises providing an interposer that includes at least one of a flex circuit or a flex cable.

15. The method of claim 13, wherein the ultrasound transducer comprises the integrated circuit, the method further comprising electrically connecting the conductive elements of the interposer to the integrated circuit using solder such that the integrated circuit is electrically connected to the acoustic elements.

16. The method of claim 13, wherein electrically connecting the conductive elements of the interposer to the acoustic elements using solder comprises:
    applying the solder to at least one of the acoustic elements or the conductive elements of the interposer; and
    curing the solder using a reflow process.

17. The method of claim 13, wherein electrically connecting the conductive elements of the interposer to the acoustic elements using solder comprises applying the solder to at least one of the acoustic elements or the conductive elements of the interposer using a stencil.

18. The method of claim 13, wherein providing an array of acoustic elements comprises providing the array of acoustic elements as a single continuous member, the method further comprising dividing the single continuous member of the acoustic elements into separate individual acoustic elements or into two or more separate groups of acoustic elements.

* * * * *